(12) United States Patent
Cumming

(10) Patent No.: US 7,763,070 B2
(45) Date of Patent: Jul. 27, 2010

(54) "W" ACCOMMODATING INTRAOCULAR LENS

(75) Inventor: J. Stuart Cumming, Laguna Beach, CA (US)

(73) Assignee: C&C Vision International Limited, Dublin (IE)

(*) Notice: Subject to any disclaimer, the term of this patent is extended or adjusted under 35 U.S.C. 154(b) by 0 days.

(21) Appl. No.: 11/940,169

(22) Filed: Nov. 14, 2007

(65) Prior Publication Data
US 2008/0154363 A1 Jun. 26, 2008

Related U.S. Application Data

(63) Continuation-in-part of application No. 11/620,488, filed on Jan. 5, 2007, which is a continuation-in-part of application No. 11/459,862, filed on Jul. 25, 2006, now abandoned.

(51) Int. Cl.
*A61F 2/16* (2006.01)
(52) U.S. Cl. .................. 623/6.37; 623/6.38; 623/6.4; 623/6.44; 623/6.46
(58) Field of Classification Search .............. 623/6.37, 623/6.44, 6.46, 6.56, 6.38, 6.4, 6.41, 6.43, 623/6.47
See application file for complete search history.

(56) References Cited

U.S. PATENT DOCUMENTS

| | | | |
|---|---|---|---|
| 4,174,543 A | 11/1979 | Kelman | |
| 4,244,060 A | 1/1981 | Hoffer | |
| 4,254,509 A | 3/1981 | Tennant | |
| 4,254,510 A | 3/1981 | Tennant | |
| 4,298,996 A | 11/1981 | Barnet | |
| 4,304,012 A | 12/1981 | Richard | |
| 4,409,691 A | 10/1983 | Levy | |
| 4,424,597 A | 1/1984 | Schlegel | |
| 4,441,217 A | 4/1984 | Cozean, Jr. | |
| 4,477,931 A | 10/1984 | Kelman | |
| 4,573,998 A | 3/1986 | Mazzocco | |
| 4,585,457 A | 4/1986 | Kalb | |
| 4,605,411 A | 8/1986 | Fedorov et al. | |
| 4,629,462 A | 12/1986 | Feaster | |
| 4,664,666 A | 5/1987 | Barrett | |
| 4,673,406 A | 6/1987 | Schlegel | |
| 4,704,123 A | 11/1987 | Smith | |

(Continued)

FOREIGN PATENT DOCUMENTS

EP    0208546 A    1/1987

(Continued)

OTHER PUBLICATIONS

Archimede Busacca, Ciliary Muscle Physiology Studied by Gonioscopy, Annals of Oculistics, vol. CLXXXVIII, Jan. 1955 (English Translation).

(Continued)

*Primary Examiner*—David H Willse
*Assistant Examiner*—Javier G Blanco
(74) *Attorney, Agent, or Firm*—Orrick, Herrington & Sutcliffe LLP

(57) ABSTRACT

An accommodating intraocular lens comprising a flexible body, a flexible optic which is moveable anteriorly and posteriorly relative to the lens body, and hinged portions longitudinally connecting the optic to the body. The body may have extending centration and fixation loops on its distal ends.

4 Claims, 5 Drawing Sheets

U.S. PATENT DOCUMENTS

| | | | |
|---|---|---|---|
| 4,718,904 A | 1/1988 | Thornton |
| 4,738,680 A | 4/1988 | Herman |
| 4,753,655 A | 6/1988 | Hecht |
| 4,759,761 A | 7/1988 | Portnoy |
| 4,778,463 A | 10/1988 | Hetland |
| 4,813,955 A | 3/1989 | Achatz et al. |
| 4,816,030 A | 3/1989 | Robinson |
| 4,840,627 A | 6/1989 | Blumenthal |
| 4,842,601 A | 6/1989 | Smith |
| 4,880,427 A | 11/1989 | Anis |
| 4,892,543 A | 1/1990 | Turley |
| 4,932,966 A | 6/1990 | Christie et al. |
| 4,932,968 A | 6/1990 | Caldwell et al. |
| 4,932,970 A | 6/1990 | Portney |
| 4,963,148 A | 10/1990 | Sulc et al. |
| 4,994,082 A | 2/1991 | Richards et al. |
| 5,047,051 A | 9/1991 | Cumming |
| 5,078,742 A | 1/1992 | Dahan |
| 5,141,507 A | 8/1992 | Parekh |
| 5,171,319 A | 12/1992 | Keates et al. |
| 5,171,320 A | 12/1992 | Nishi |
| 5,217,490 A | 6/1993 | Sayano et al. |
| 5,275,624 A | 1/1994 | Hara et al. |
| 5,376,115 A | 12/1994 | Jansen |
| 5,476,514 A | 12/1995 | Cumming |
| 5,496,366 A | 3/1996 | Cumming |
| 5,522,891 A | 6/1996 | Klaas |
| 5,578,078 A | 11/1996 | Nakajima et al. |
| 5,674,282 A | 10/1997 | Cumming |
| 6,051,024 A | 4/2000 | Cumming et al. |
| 6,129,760 A | 10/2000 | Fedorov et al. |
| 6,193,750 B1 | 2/2001 | Cumming |
| 6,197,059 B1 | 3/2001 | Cumming |
| 6,231,603 B1 | 5/2001 | Lang et al. |
| 6,387,126 B1 | 5/2002 | Cumming |
| 6,494,911 B2 | 12/2002 | Cumming |
| 6,503,276 B2 | 1/2003 | Lang et al. |
| 6,540,353 B1 | 4/2003 | Dunn |
| 6,551,354 B1 | 4/2003 | Ghazizadeh et al. |
| 6,554,859 B1 | 4/2003 | Lang et al. |
| 6,558,419 B1 | 5/2003 | Pham et al. |
| 6,638,306 B2 | 10/2003 | Cumming |
| 6,660,035 B1 * | 12/2003 | Lang et al. | 623/6.37 |
| 6,749,634 B2 * | 6/2004 | Hanna | 623/6.37 |
| 6,767,363 B1 | 7/2004 | Bandhauer |
| 6,896,029 B2 | 9/2004 | Callahan et al. |
| 6,818,158 B2 | 11/2004 | Pham et al. |
| 6,849,091 B1 * | 2/2005 | Cumming | 623/6.21 |
| 7,018,409 B2 | 3/2006 | Glick et al. |
| 7,048,760 B2 | 5/2006 | Cumming |
| 7,150,760 B2 | 12/2006 | Zhang |
| 2001/0001836 A1 | 5/2001 | Cumming |
| 2002/0128710 A1 | 9/2002 | Eggleston |
| 2003/0060880 A1 | 3/2003 | Feingold |
| 2003/0187505 A1 | 10/2003 | Liao |
| 2004/0002757 A1 | 1/2004 | Lai et al. |
| 2006/0116764 A1 | 6/2006 | Simpson |
| 2006/0259140 A1 | 11/2006 | Dell |

FOREIGN PATENT DOCUMENTS

| | | |
|---|---|---|
| EP | 0336877 A1 | 10/1989 |
| EP | 0941717 A | 9/1999 |
| FR | 1103399 | 11/1955 |
| GB | 2171912 A | 9/1986 |
| WO | WO 95/06446 | 3/1995 |
| WO | WO 96/15734 A2 | 5/1996 |
| WO | WO 96/25126 A1 | 8/1996 |
| WO | WO 01/97742 A2 | 12/2001 |
| WO | WO 2004046768 A2 | 6/2004 |

OTHER PUBLICATIONS

Archimede Busacca, La Physiologid Du Muscle Ciliarire Etudiee par la Gonioscopie, Annales D'Oculistique, vol. CLXXXVIII, 1st Livraison, Janvier 1955 (French Translation).

D. Jackson Coleman, M.D., On the Hydraulic Suspension Theory of Accommodation, Tr. Am. Opth. Soc. vol. LXXXIV, pp. 846-868, 1986.

J. Stuart Cumming, M.D., Accommodating Intra-Ocular Lens Development & Clinical Results, PowerPoint presentation 1999-2000.

Spencer Thornton, "Accommodating in Pseudophakia," Color Atlas of Lens Implantation, Chapter 25, pp. 159-161.

Lee, Judith, "Update on IOLs," Outpatient Surgery (Mar. 2002), printed Oct. 26, 2004 (http://www.outpatientsurgery.net/2002/os03/f4.shtml).

Zhang, Z. et al., "A clinical study of posterior capsular opacification after implantation of foldable intraocular lenses with different edges of optics," Zhonghua Yan Ke Za Zhi 38(10):606-609 (Oct. 2002), printed Oct. 26, 2004 (http://www.ncbi.nlm.nih.gov/entrez/query.fcgi?cmd=Retrieve&db=pubmed&dopt=Abstract&list...).

Masket, Samuel, "Continuing Medical Education: Oct. 2003 IOL Edge Design, and PCO Dysphotopsia," Review of Ophthalmology, printed Oct. 26, 2004 (http://www.revophth.com/index.asp?ArticleType=SiteSpec&page=cme/oct03/lesson.htm).

Sabbagh, Leslie, "IOL Design Closes Off PCO," Review of Ophthalmology, printed Oct. 26, 2004 (http://www.revophth.com/index.asp?page=1_255.htm).

* cited by examiner

Anterior

Posterior

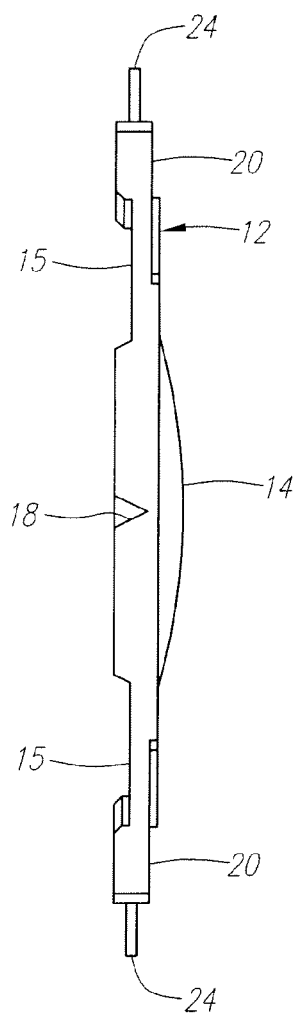
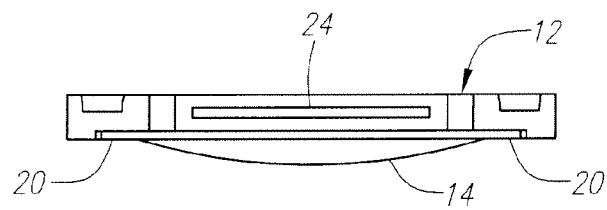
FIG. 5
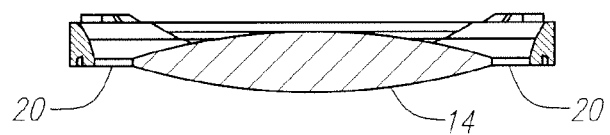
FIG. 6
FIG. 4
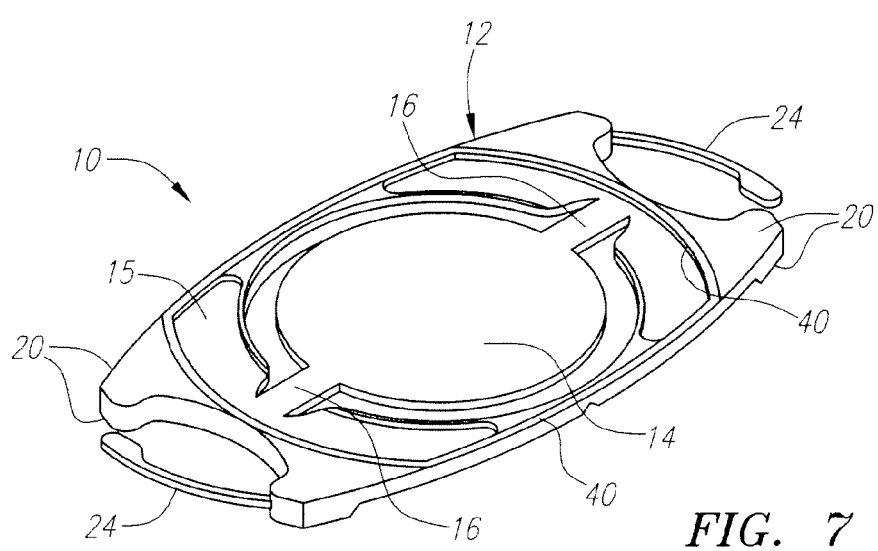
FIG. 7

"W" ACCOMMODATING INTRAOCULAR LENS

This application is a continuation-in-part of application Ser. No. 11/620,488 filed Jan. 5, 2007, which is a continuation-in-part of Ser. No. 11/459,862 filed on Jul. 25, 2006 now abandoned, both of which are fully incorporated herein by reference.

BACKGROUND

Intraocular lenses have for many years had a design of a single optic with loops attached to the optic to center the lens and fixate it in the empty capsular bag of the human eye. In the mid '80s plate lenses were introduced, which comprised a silicone lens, 10.5 mm in length, with a 6 mm optic. These lenses could be folded but did not fixate well in the capsular bag, but resided in pockets between the anterior and posterior capsules. The first foldable lenses were all made of silicone. In the mid 1990s an acrylic material was introduced as the optic of lenses. The acrylic lens comprised a biconvex optic with a straight edge into which were inserted loops to center the lens in the eye and fixate it within the capsular bag.

Recently accommodating intraocular lenses have been introduced to the market, which generally are modified plate haptic lenses. A plate haptic lens may be defined as an intraocular lens having two or more plate haptics where combined junctions with the optic represent one quarter or more of the circumference of the optic.

Flexible acrylic material has gained significant popularity among ophthalmic surgeons. In 2003 for example more than 50% of the intraocular lenses implanted had acrylic optics. Hydrogel lenses have also been introduced. The acrylic materials are incapable of multiple flexions without fracturing.

The advent of an accommodating lens which functions by moving the optic along the axis of the eye by repeated flexions somewhat limited the materials from which the lens could be made. Silicone is the ideal material, since it is flexible and can be bent probably several million times without showing any damage. Additionally one or more grooves or hinges can be placed across the plate adjacent to the optic as part of the lens design to facilitate movement of the optic relative to the outer ends of the haptics. An example accommodating lens of this nature is disclosed in U.S. Pat. No. 6,387,126 in the name of J. Stuart Cumming.

SUMMARY OF THE INVENTION

According to the present invention a new form of accommodating intraocular lens having a lens body and optic is provided with plural straps, preferably two, between the optic and lens body to allow the optic to move anteriorly and posteriorly in response to the pressure gradient created with accommodation. The lens body preferably has a central hinge. The structure is such that it particularly benefits from changes in vitreous pressure with accommodation.

The lens body is shaped such that it is wider centrally than it is on its peripheral end. The end of the lens body, after implantation into the eye, is held in position by a pocket formed by fusion of the anterior and posterior bag walls. Upon ciliary muscle constriction the zonules attaching the capsular bag to the ciliary muscle relax and the vitreous pressure increases. The hinged lens body surrounding the optic cannot move peripherally into the smaller pocket. The fibrosed capsular bag thus exerts end to end pressure on the ends of the posteriorly vaulted lens, pushing the posteriorly vaulted two lens body parts back into the vitreous further increasing the vitreous cavity pressure. This increase in pressure plus the increase caused by cilary muscle contraction with redistribution of its mass, urges the optic forward. The thin straps and thus hinges, especially the base of the hinges, stretch like a rubber band further facilitating anterior movement of the lens (See. FIG. 9).

Thus, it is a feature of the present invention to provide a new form of accommodating lens.

BRIEF DESCRIPTION OF THE DRAWINGS

FIG. 4 is a side view.

FIG. 5 is an end view.

FIG. 6 is a cross-sectional view along lines 6-6 of FIG. 2.

FIG. 7 is a perspective view of the back or posterior side of the lens.

DESCRIPTION OF PREFERRED EMBODIMENT

Figure 1A:
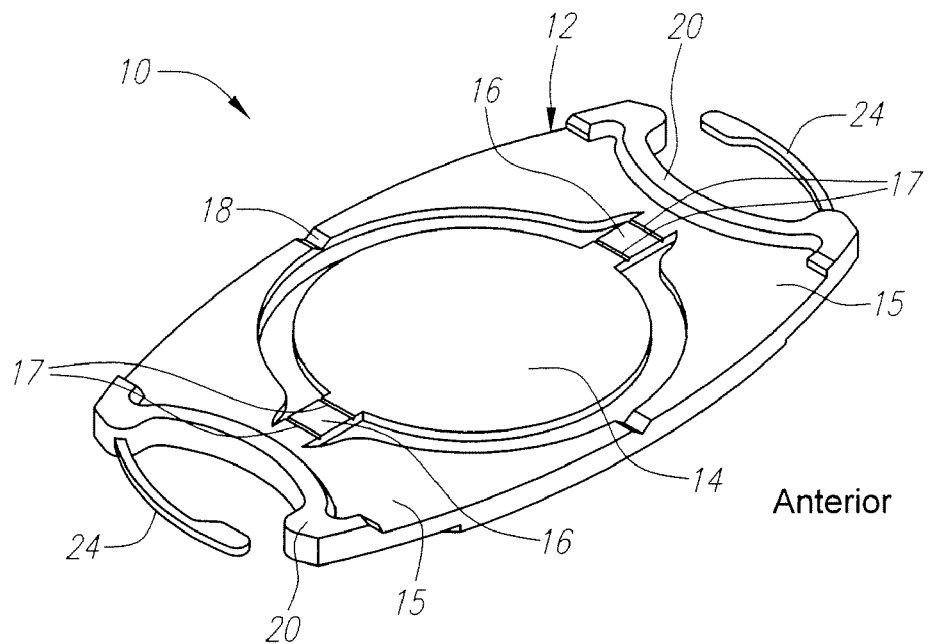
FIG. 1a is a prospective view of the front or anterior side of the lens according to the present invention.

Turning now to the drawings, FIG. 1a is a perspective view of the present lens 10 including a lens body or plate 12 and optic 14. The body 12 includes haptics 15 which are wider centrally thus preventing them from moving peripherally into a smaller bag pocket upon ciliary muscle contraction. The body 12 and optic 14 are formed of silicone or other suitable flexible material. Straps 16 are provided between the body 12 and the periphery or outer diameter of the optic 14. Each strap preferably includes one or two hinges 17 on the anterior side of the lens, or no hinges. The straps may be 0.5 mm long in the radial direction and 0.25 mm thick to support the optic 14 by the straps 16. The optic 14 typically can have a diameter of 4.5-5.0 mm, a typical width of the overall lens 10 on the short side is 6.1 mm and the typical length from end to end (not including fixation fingers) on the long side is 10.5-11.5 mm. A typical optic thickness is 0.4-1.3 mm.

The body 12 and optic 14, as well as outer thickened footplate ends 20, are formed of silicone or other suitable flexible material. The lens 10 also preferably includes fixation loops 24 of polymide or similar material. A typical outer loop-to-loop length is 11.0-12.5 mm. The thickened ends 20 fully engulf the fixation loops 24 in the silicon thus to provide a strong matrix to hold the loops 24. There is an additional function of these thickened areas of the plate. They also serve to elevate the anterior capsule of the human lens away from the optic and from the posterior capsule after the cataract has been removed and the lens implanted. This may serve to reduce capsular opacification and contraction. The haptics 15 can be any typical shape, such as in the present Figures, rectangular, triangular, or the like.

Figure 1B:
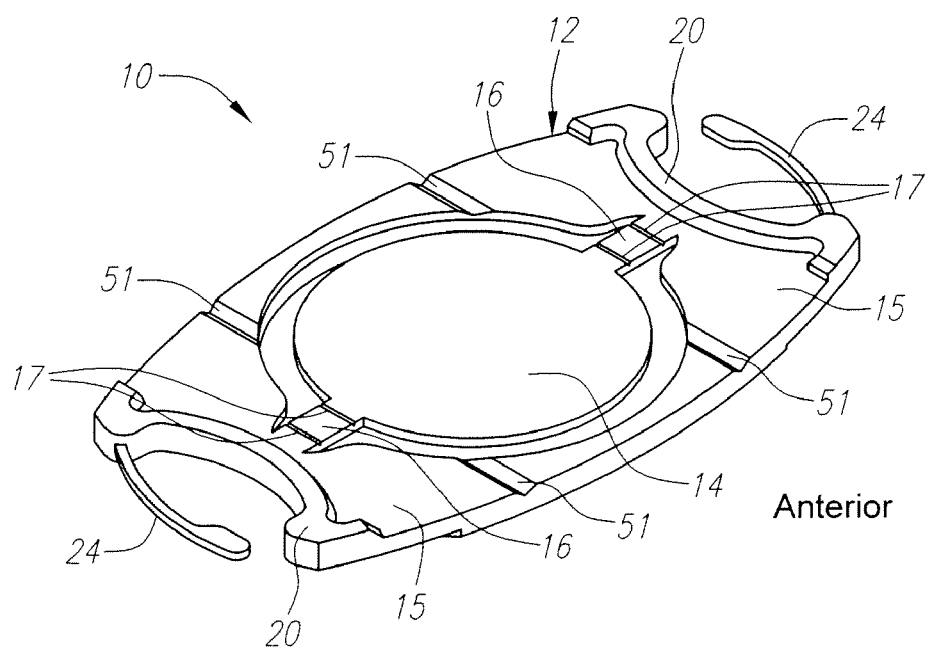
FIG. 1b is a prospective view of an alternative embodiment.
Figure 2:
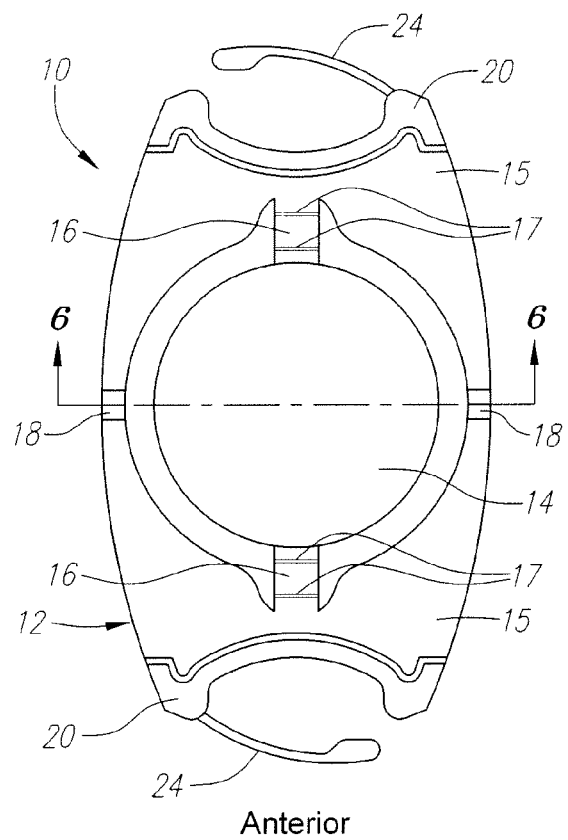
FIG. 2 is a plan view of the anterior side.

The straps 16 and hinges 17 function by allowing the optic to move anteriorly and posteriorly. The approximately 1.0-2.0 mm wide straps are a point of relative weakness in the plane of the lens body 12 encircling the optic 14, thereby allowing the entire optic 14 to herniate forward (anteriorly)

from its far posterior position in a translational forward movement. This feature is enhanced by keeping the mass of the optic 14 to a minimum as described below. This new mechanism may boost the effect of the other features of the lens. Rather than a fluid-filled sac pushing through an aperture as in some prior lenses, the present lens involves a deformable solid optic moving anteriorly and posteriorly through a hinged area 16 in the plate or body 12. Central hinges 18 on the anterior side of the body 12 hinging the haptics 15 further facilitate movement of the optic with ciliary muscle contraction. FIG. 1*b* shows an alternative embodiment with a pair of hinges 51 as shown in alignment with the edges of the optic rather than the hinges 18.

Figure 9:
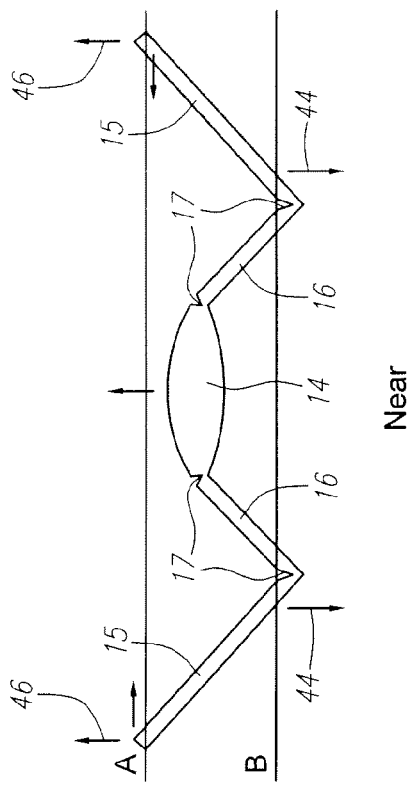
FIG. 9 is a side view during near vision.
Figure 8:
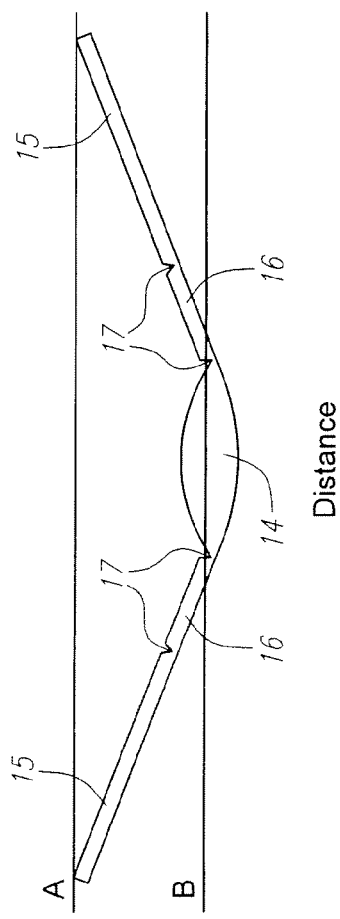
FIG. 8 is a side view during distance vision.
Figure 10:
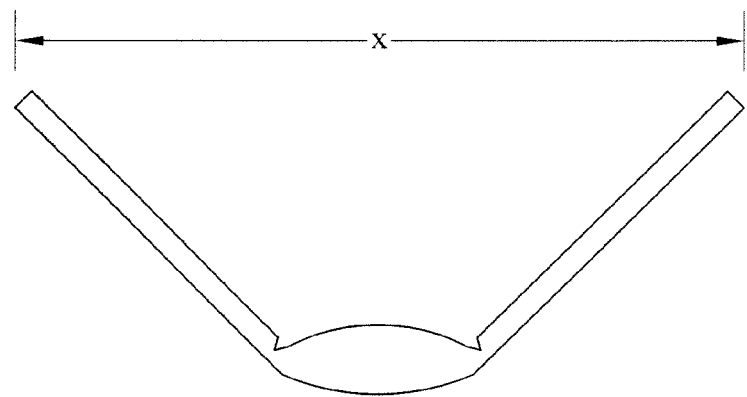
FIGS. 10-12 illustrate a "W" concept with FIG. 10 showing a conventional lens, and FIGS. 11-12 generally illustrating the present lens with a wide hinge base and additional hinges to allow the lens to move to a "W" shape.
Figure 11:
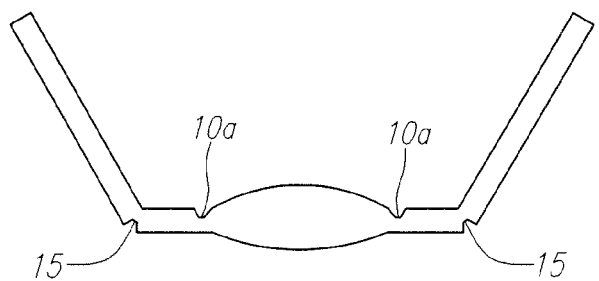
Figure 12:
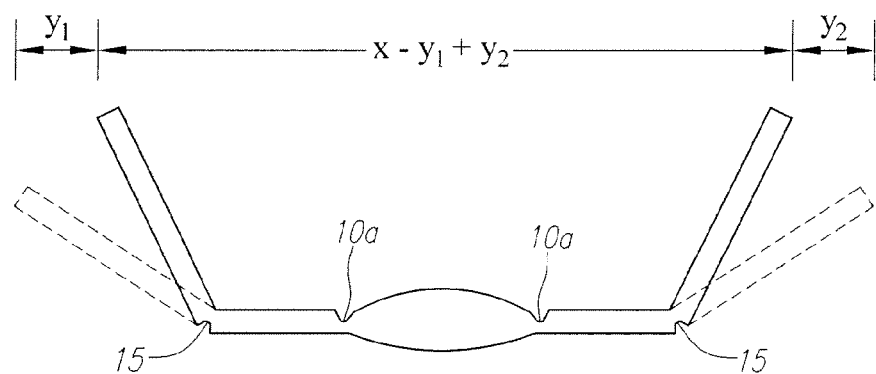

Of significance is the manner in which the optic 14 and haptic plates 15 move in accommodating from distance to near vision and this is particularly illustrated in FIGS. 8 and 9 with respect to anterior A and posterior B reference lines in these Figs. As is usual, the ends of the haptics 15 or the loops 24 as the case may be are implanted in the capsular bag such that the optic 14 is vaulted posteriorly for distance vision as seen in FIG. 8. The optic 14 moves anteriorly for near vision as shown in FIG. 9 upon ciliar muscle contraction. In particular, the whole lens moves forward a little as seen in FIG. 9 and the haptic plates 15 move centrally and backward slightly in the direction of arrows 44 which results in a pressure caused by ciliary muscle contraction to further increase pressure on the optic 14 that pushes the optic further forward because the hinge or hinges 17 are thin and stretch a little and the optic deforms somewhat. This provides an increase in anterior optic movement with optic deformation. Also, the ends of the haptics 15 push backward against the posterior capsule as indicated by arrows 46 in FIG. 9 with increases of vitreous pressure.

The width of the hinges is 1.0-3.0 mm and the thickness of 0.1-0.3 mm.

Another feature allowing the present lens to accommodate is that the optic 14 can be deformable and may be constructed with a lower durometer than previously built into any lens. The surrounding plate 12 preferably is made of a higher, standard durometer material, similar to the eyeonics Inc. AT45 lens (which is durometer 48). The optic 14 itself is not required to contribute to the structural stability of the lens and, therefore, the optic 14 can be extremely soft. In addition to forward axial translation, the bending or deformation of the optic 14 with accommodation will induce power change. This may result in the bending of the optic to be accentuated. This feature is further enhanced by maintaining the optic very thin since a thinner optic will bend more than a thick optic for any given level of force applied. An example range of optic 14 center thicknesses is about 0.4 mm to 1.3 mm for a diopter range of 10 to 33. A typical common diopter of the optic of the present lens is 22 diopters and which has a thickness of 0.73 mm. As a comparison, the AT 45 noted earlier in a 22 diopter has a thickness of 0.88 mm, and a newer AT-45SE is 0.98 mm.

A 4.5 mm diameter optic 14 and with a reduced edge thickness of 0.1 to 0.2 mm for example can be provided. The index of refraction can be increased and this will accentuate this feature even further.

The present lens can be easily foldable with forceps or an injector. A pre-loaded system is preferable.

Figure 3:
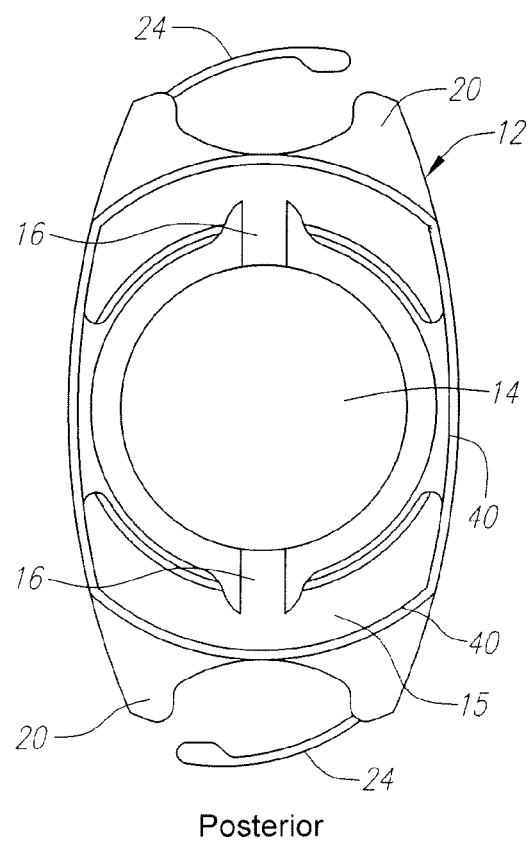
FIG. 3 is a plan view of the back or posterior side of the lens.

An additional feature is the incorporation of a ridge or ridges 40 on the back surface (posterior side) of the plate 12 and/or haptic arm as the case may be as seen in FIGS. 3 and 7. These ridges traverse the plate and completely encircle the optic around the perimeter of the lens body. There is an additional ridge central to the first ridge traversing the plate adjacent to the optic straps. The purpose of these ridges is to prevent proliferation of lens epithelial cells into the area behind the plate or optic. For plate lenses this can dramatically reduce the incidence of capsular contraction. Epithelial cells will be prevented from migrating under the plate and undergoing a fibrotic contraction. Furthermore, the square edge of the loops, plate haptics and the square edge of the optic further protect against cells migrating in from the sides of the plate.

While an embodiment of the present invention as been shown and described, various modifications may be made without departing from the scope of the present invention, and all such modifications and equivalents are intended to be covered.

What is claimed is:

1. An uniplanar accommodating intraocular lens comprising a flexible lens optic and a flexible longitudinal lens body having a longitudinal axis, said flexible longitudinal lens body defined by flat plate haptics having a pair of centrally located V-shaped hinges transverse to said longitudinal axis, the lens body asymmetrically completely surrounding the periphery of the flexible lens optic, the optic being suspended from a small part of its periphery by two thin hinged straps connected to the lens body, each strap includes at least one hinge formed on the anterior side of the intraocular lens, the straps being approximately 0.5 mm long radially and approximately 0.25 mm thick and oriented along the longitudinal axis of the longitudinal lens body, the body being constructed such that upon contraction of the ciliary muscle of the eye the lens body adjacent to the optic moves backward relative to the flexible optic, and the longitudinal lens body having attached at ends thereof open loops of a material different from the lens body to form fixation and centration fingers.

2. A lens as in claim 1 wherein the lens body is wider centrally.

3. A lens as in claim 1 wherein each strap has two hinges, each one on a different side of the strap.

4. A lens as in claim 1 wherein a posterior side of the body includes a ridge.

* * * * *